(12) United States Patent
Shiao

(10) Patent No.: US 10,517,640 B2
(45) Date of Patent: Dec. 31, 2019

(54) MICRO-IMPLANTER FOR HAIR FOLLICLE

(75) Inventor: I-Sen Shiao, Taipei (TW)

(73) Assignee: Follicular Technologies, LLC, Los Angeles, CA (US)

( * ) Notice: Subject to any disclaimer, the term of this patent is extended or adjusted under 35 U.S.C. 154(b) by 750 days.

(21) Appl. No.: 11/480,965

(22) Filed: Jul. 6, 2006

(65) Prior Publication Data

US 2008/0009896 A1    Jan. 10, 2008

(51) Int. Cl.
*A61B 17/34* (2006.01)
*A61B 17/00* (2006.01)

(52) U.S. Cl.
CPC .............. *A61B 17/3468* (2013.01); *A61B 2017/00752* (2013.01)

(58) Field of Classification Search
CPC .......................................... A61B 2017/00752
USPC ....... 606/131–133, 167, 172, 185, 189, 187; 623/15.11, 15.12
See application file for complete search history.

(56) References Cited

U.S. PATENT DOCUMENTS

| | | | | |
|---|---|---|---|---|
| 3,596,292 A | * | 8/1971 | Erb et al. | 623/15.11 |
| 3,699,969 A | * | 10/1972 | Allen | 606/187 |
| 4,126,124 A | * | 11/1978 | Miller | 606/187 |
| 4,473,076 A | * | 9/1984 | Williams et al. | 606/172 |
| 5,423,825 A | * | 6/1995 | Levine | 606/86 R |
| 5,584,841 A | * | 12/1996 | Rassman | 606/132 |
| 5,643,308 A | * | 7/1997 | Markman | 606/187 |
| 5,782,851 A | * | 7/1998 | Rassman | A61B 17/32093 606/132 |
| 5,817,120 A | * | 10/1998 | Rassman | 606/187 |

* cited by examiner

*Primary Examiner* — Anh T Dang
(74) *Attorney, Agent, or Firm* — Venable LLP

(57) ABSTRACT

A micro-implanter for hair follicle includes a plunger and a hair follicle holding tube coaxially fitted around the plunger. A hair follicle may be positioned in the hair follicle holding tube below the plunger. The plunger is provided at a lower end with a stopper for limiting a depth by which the hair follicle is implanted into a mini implanting slit cut on a bald scalp. The hair follicle holding tube has a lower end formed into a tapered and narrowed section to facilitate easy insertion of the hair follicle holding tube into the mini implanting slit. When the hair follicle holding tube has been inserted into the mini implanting slit on the scalp, the plunger may be pushed forward to implant the hair follicle into the mini implanting slit.

2 Claims, 6 Drawing Sheets

MICRO-IMPLANTER FOR HAIR FOLLICLE

FIELD OF THE INVENTION

The present invention relates to a hair implanter, and more particularly to a micro-implanter for hair follicle that facilitates quick implanting of a hair follicle into a bald scalp to avoid damage, breaking, and death of the hair follicle during the implantation.

BACKGROUND OF THE INVENTION

The hair implantation technique has been largely improved over the past decade. A so-called microscopic hair follicle implantation technique has been widely employed throughout the world to treat male patterned baldness, i.e. Androgenetic Alopecia. In this hair implantation technique, each hair follicle is independently implanted into the scalp. The hair follicles used in the microscopic hair implantation are relocated from a donor site, which is usually a back of the head, to a balding area of the patient's scalp. Each hair follicle normally has one to four hairs, as shown in FIG. 1. And, each hair follicle has a diameter about 1-2 mm, and a length about 6-7 mm, and is therefore very tiny and soft.

There are various kinds of hair implanters available in the market. However, most of the currently available hair implanters have big volume and are not suitable for use in the microscopic hair follicle implantation. Up to date, hair follicles are implanted by a surgeon using forceps. That is, the surgeon uses forceps to clip a root portion of the hair follicle, and forces the hair follicle into an implanting hole pierced on the bald scalp. The implanting hole is usually formed by piercing the bald scalp using a needle, which normally has a small gage number of 18 or 19. Therefore, the implanting hole is very small in size. It is uneasy to force a hair follicle into such a small hole. The hair follicle would very possibly be damaged by the forceps, or become broken or dead in the course of forceps implantation when it could not be successfully implanted into the tiny implanting hole for several times. The tight clipping of the hair follicle with the forceps would also cause follicle death. These are the difficulties often encountered by the surgeons in the microscopic hair follicle implantation.

It is therefore tried by the inventor to develop a micro-implanter for hair follicle to solve the problems encountered in the existing microscopic hair follicle implantation.

SUMMARY OF THE INVENTION

A micro-implanter for hair follicle according to the present invention includes a plunger and a hair follicle holding tube coaxially fitted around the plunger. A hair follicle is positioned in the hair follicle holding tube below the plunger. The plunger is provided at a lower end with a stopper, which is guided by an axial open slot on the hair follicle holding tube to move upward and downward for limiting a depth by which the hair follicle is implanted into a mini implanting slit cut on a bald scalp. The hair follicle holding tube has a lower end formed into a tapered and narrowed section to facilitate easy insertion of the hair follicle holding tube into the mini implanting slit. When the hair follicle holding tube has been inserted into the mini implanting slit on the scalp, the plunger may be pushed forward to completely implant the hair follicle into the mini implanting slit. In this manner, the hair follicle is protected against damage, breaking or death in the course of implantation, because there is no forceps to clip the root portion of the hair follicle.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein FIG. 1 schematically shows that each hair follicle has one to three hairs.

DETAILED DESCRIPTION OF THE PREFERRED EMBODIMENTS

Figures 1, 2:
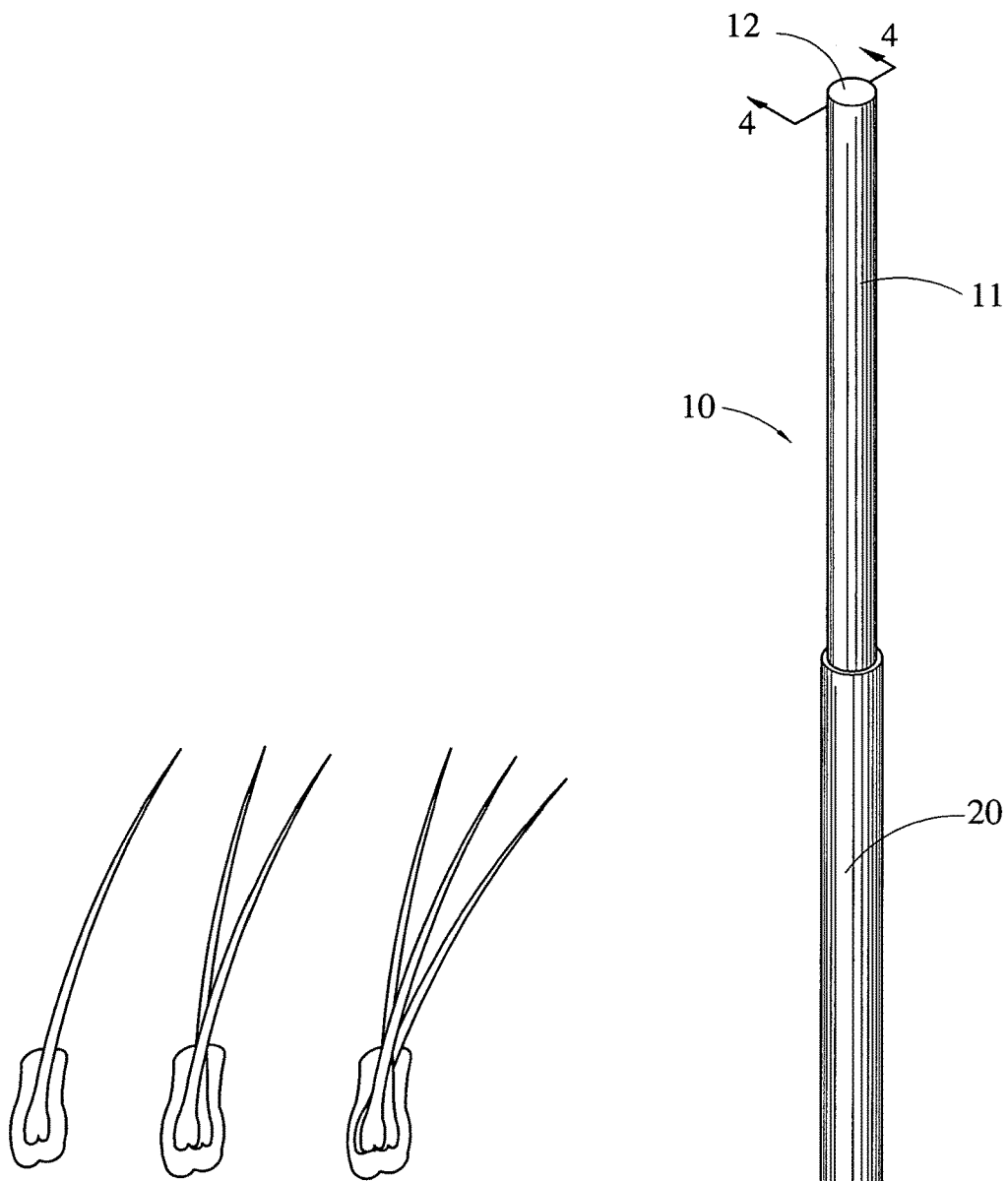
FIG. 2 is an assembled perspective view of a micro-implanter for hair follicle according to a preferred embodiment of the present invention.
Figure 3:
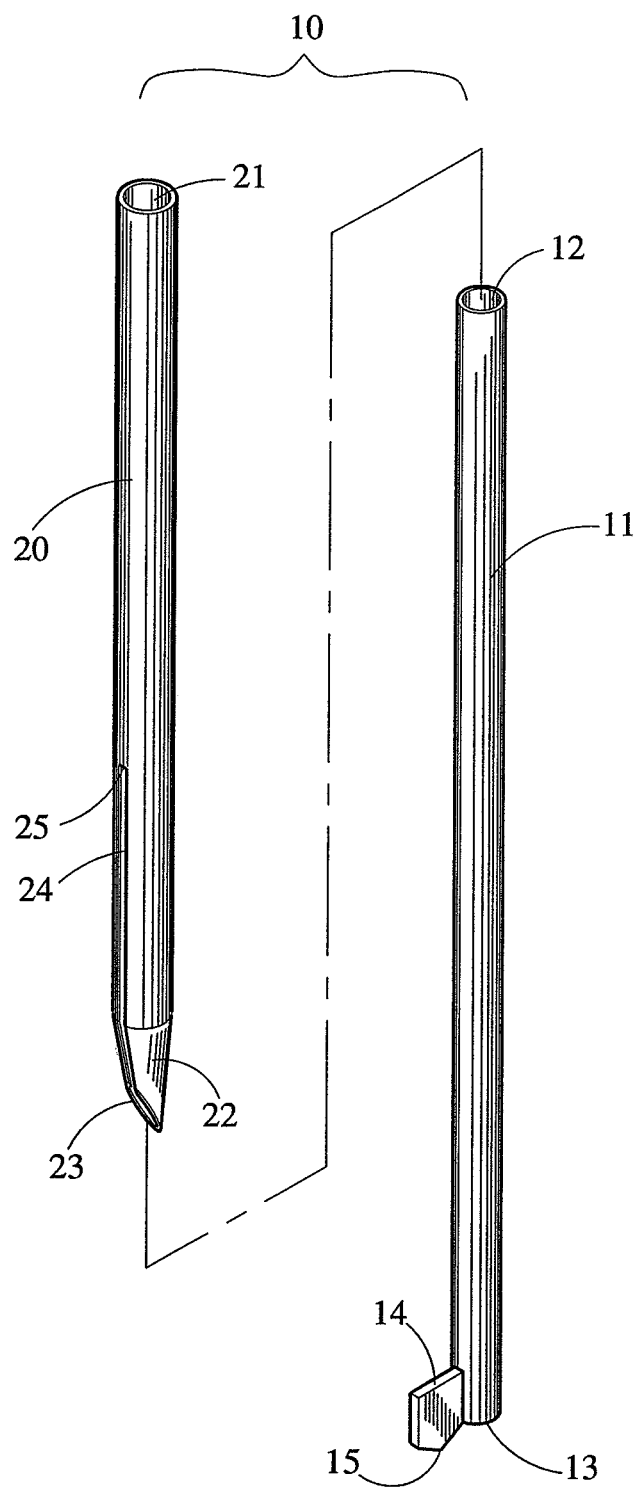
FIG. 3 is an exploded perspective view of the micro-implanter for hair follicle of the present invention.

Please refer to FIGS. 2 through 5, in which a micro-implanter for hair follicle 10 according to a preferred embodiment of the present invention is shown. The micro-implanter for hair follicle 10 of the present invention is made of a non-toxic tough plastic material, such as polypropylene, or a stainless steel material. As shown in the illustrated drawings, the micro-implanter for hair follicle 10 includes a plunger 11 and a hair follicle holding tube 20. The plunger 11 has a round cross section, and includes an upper end 12 and a lower end 13. The lower end 13 of the plunger 11 has a radially outward projected stopper 14, which has a tapered bottom 15. The stopper 14 with the tapered bottom 15 has the function of limiting a depth by which a hair follicle 30 is implanted into a mini implanting slit 32 on a bald scalp 31, and preventing the plunger 11 from skidding off the bald scalp 31, as shown in FIG. 6B.

The hair follicle holding tube 20 defines an axial bore 21 for receiving the plunger 11 therein, so that the plunger 11 may be moved in the hair follicle holding tube 20 toward or away from the scalp 31. A lower end of the hair follicle holding tube 20 is formed into a tapered and narrowed section 22 with a beveled surface 23 provided at an outermost end of the tapered and narrowed section 22, so that the hair follicle holding tube 20 may be quickly inserted into the mini implanting slit 32 on the bald scalp 31, as shown in FIG. 6B. The hair follicle holding tube 20 is provided with an open slot 24 axially upward extended from the lower end of the tapered and narrowed section 22 by a predetermined distance, so that the stopper 14 of the plunger 11 is guided by the open slot 24 to move upward and downward along the hair follicle holding tube 20.

Figure 4:
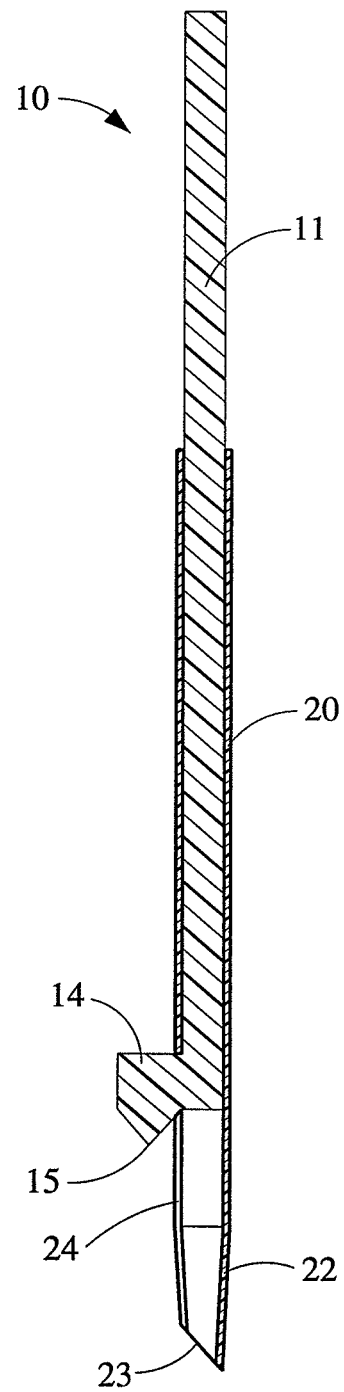
FIG. 4 is a sectional view taken along line 4-4 of FIG. 2.
Figure 6C:
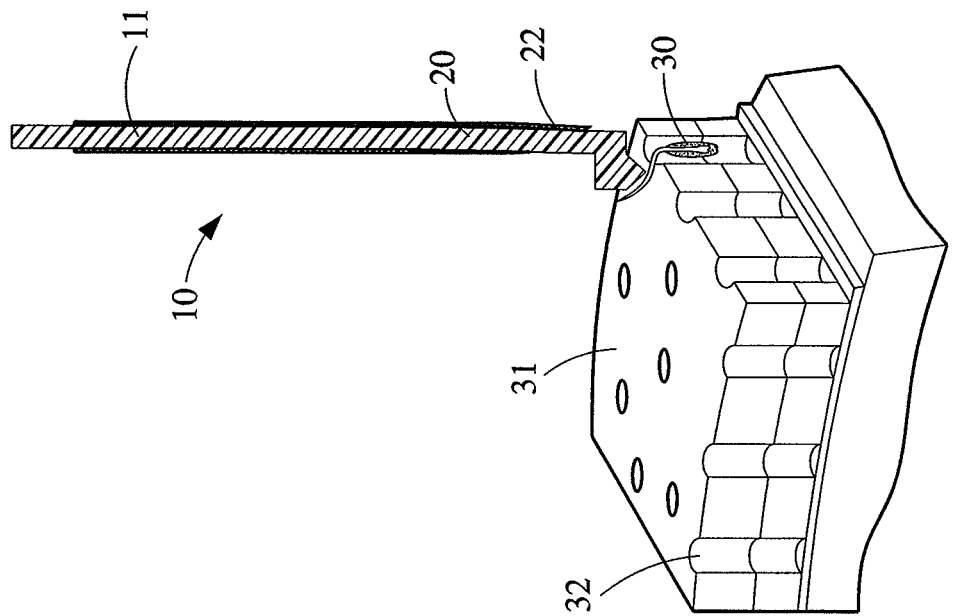

As can be seen from FIG. 4, the plunger 11 is initially located at a retracted position in the hair follicle holding tube 20, with the stopper 14 abutted on a flat upper end 25 of the open slot 24. When the tapered and narrowed section 22 of the hair follicle holding tube 20 is inserted into the mini implanting slit 32, as shown in FIG. 6B, a force is applied to the upper end of the plunger 11 to move the plunger 11 forward from the retracted position shown in FIG. 4, bringing the stopper 14 to move forward along the open slot 24. The lower end of the plunger 11 would push the hair follicle 30 held in the lower end of the tube 20 toward the scalp 31, until the tapered bottom 15 of the stopper 14 is in contact with the scalp 31, as shown in FIG. 6C. In this manner, the hair follicle 30 could be completely implanted in the mini implanting slit 32. The tapered bottom 15 of the stopper 14 contacting with the scalp 31 functions to limit the depth by which the hair follicle 30 is implanted into the mini implanting slit 32.

Figures 5, 6A:
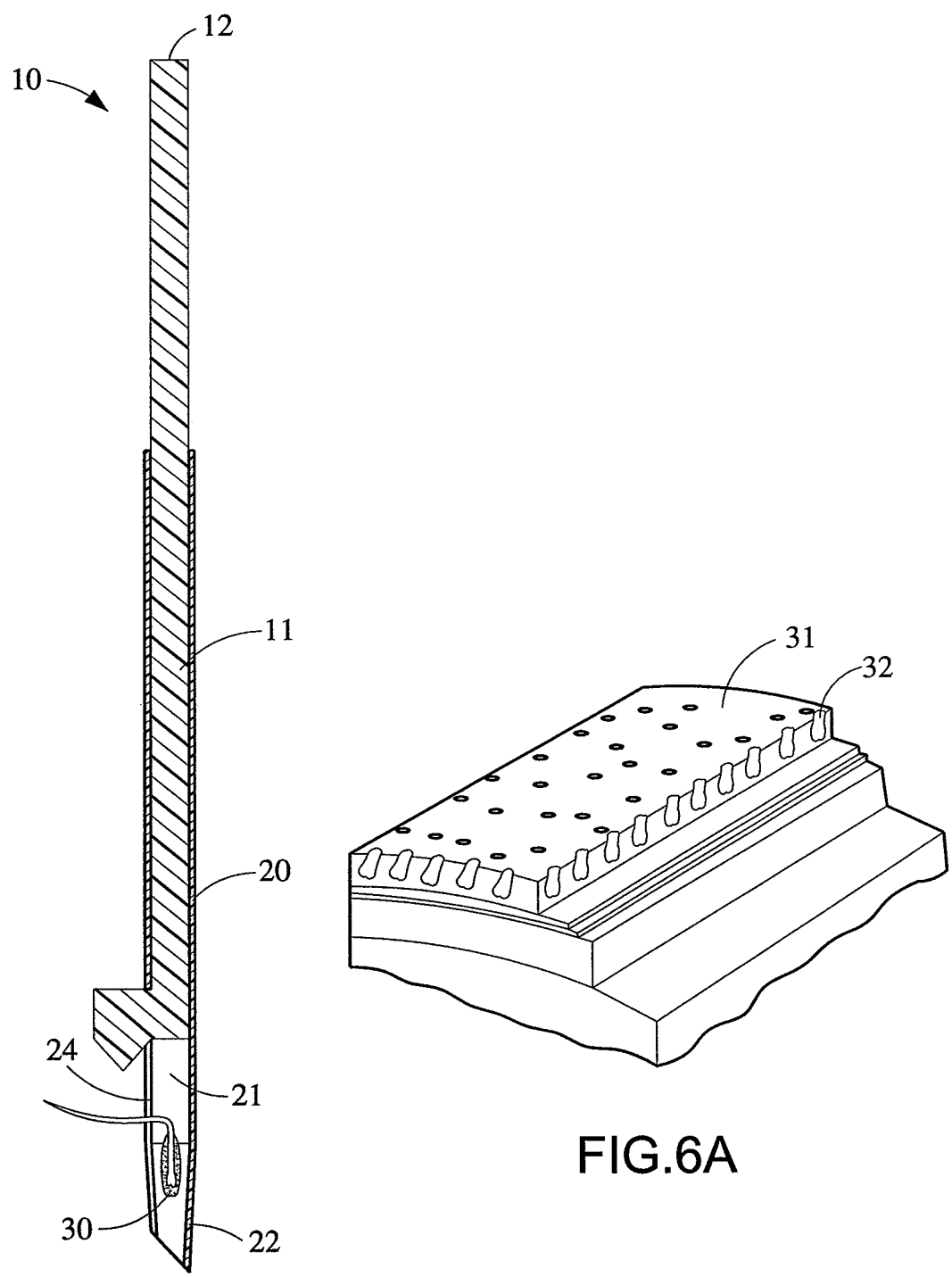
FIG. 5 is a sectional view of the micro-implanter for hair follicle of the present invention with one hair follicle held therein.
FIGS. 6A to 6D show the steps of implanting the hair follicle to a scalp using the micro-implanter for hair follicle of the present invention.
Figure 6B:
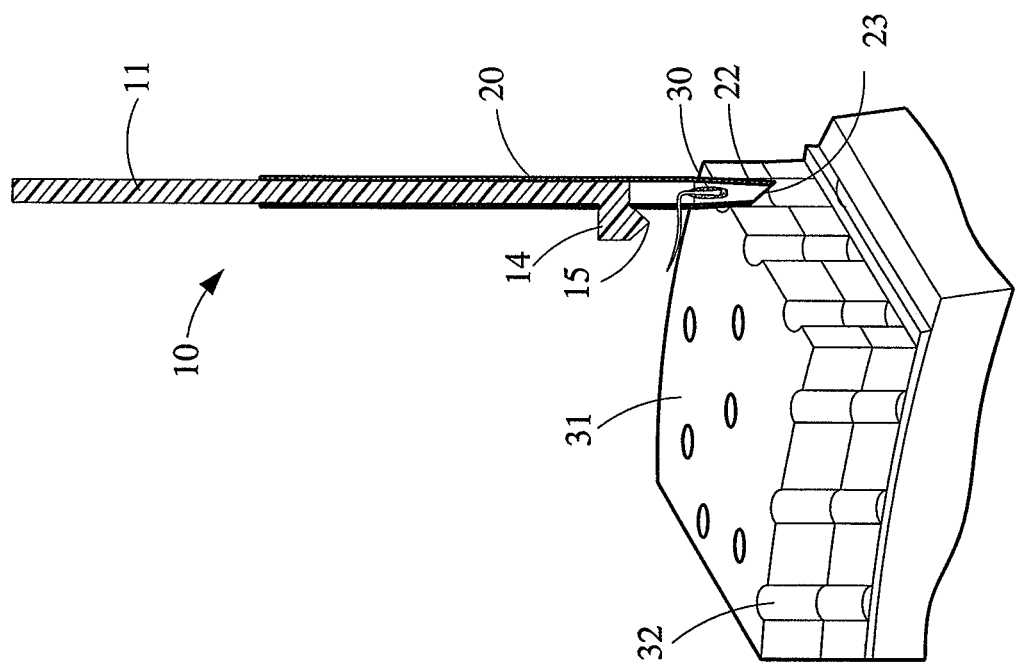

Please refer to FIG. 5. The hair follicle 30 is positioned in the bore 21 by using forceps to hold the epithelium of the hair follicle 30 and moving the hair follicle 30 along the open slot 24 of the hair follicle holding tube 20 into the bore 21 to locate below the plunger 11.

Figure 6D:
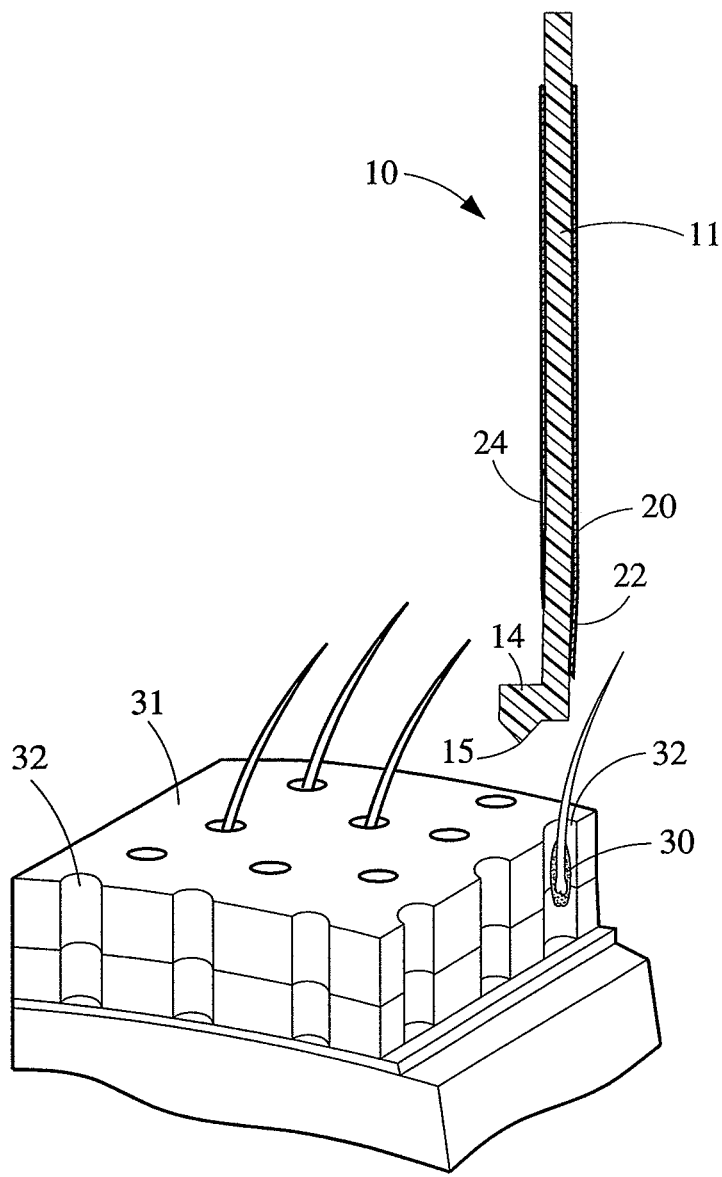

FIGS. 6A to 6D show the steps of using the micro-implanter for hair follicle 10 of the present invention to implant hair follicles into a bald scalp 31. In Step 1, a plurality of mini implanting slits 32 are cut on a bald scalp 31, as shown in FIG. 6A. In Step 2, an insertion force is applied to one hair follicle holding tube 20 to insert the tapered and narrowed section 22 thereof into one of the mini implanting slits 32, so that a hair follicle 30 held in the lower end of the hair follicle holding tube 20 is implanted into the mini implanting slit 32; and the plunger 11 is pushed toward the scalp 31 until the tapered bottom 15 of the stopper 14 is in contact with the scalp 31, as shown in FIG. 6B. In Step 3, the hair follicle holding tube 20 is extracted from the mini implanting slit 32 while the hair follicle 30 is left at a predetermined position in the mini implanting slit 32, as shown in FIG. 6C. And, in Step 4, the plunger 11 is withdrawn from the scalp 31, and the hair follicle 30 is completely implanted into the mini implanting slit 32, as shown in FIG. 6D.

Figure 7:
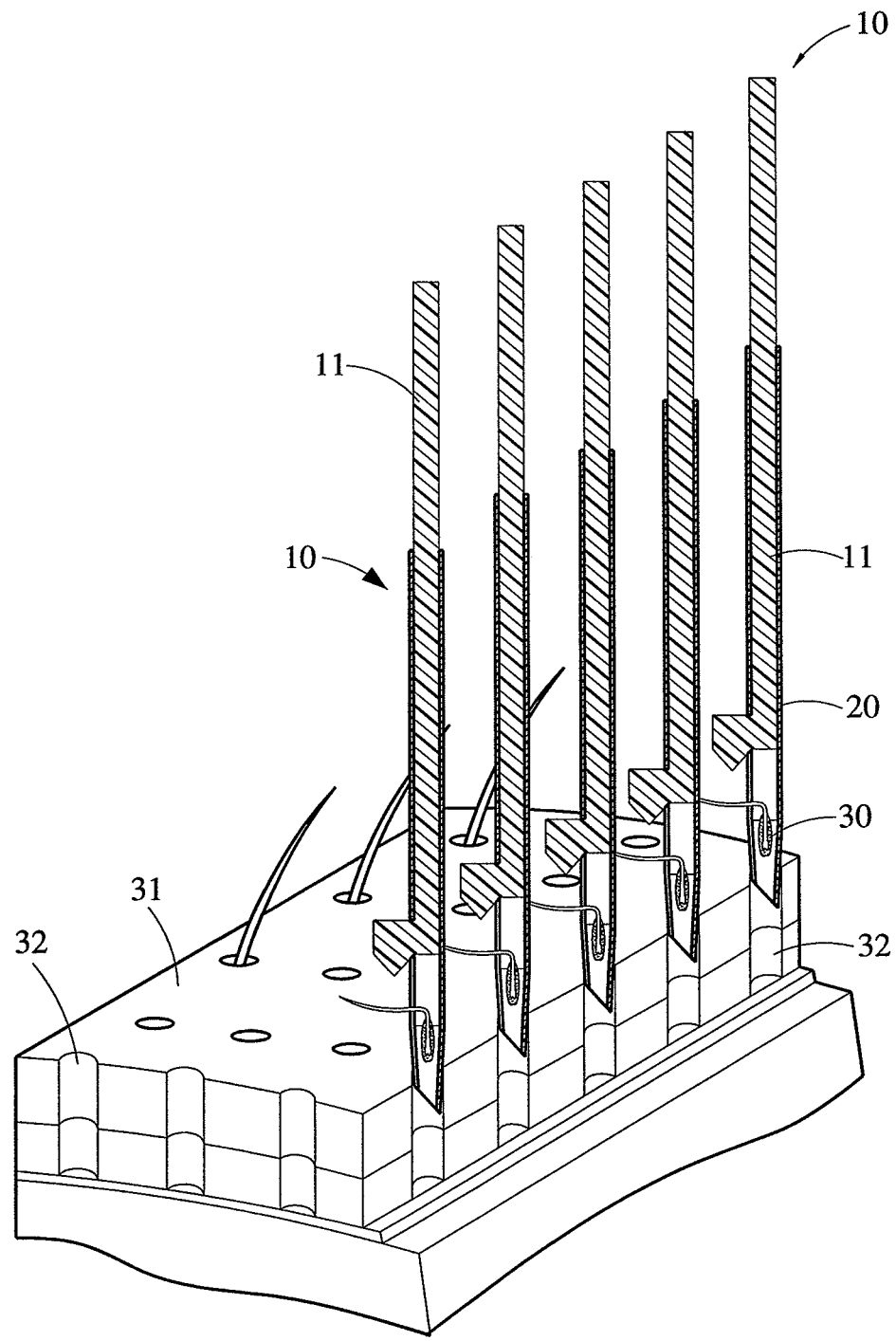
FIG. 7 is a perspective view showing a plurality of micro-implanter for hair follicles of the present invention having the hair follicle held therein are used at the same time to implant multiple hair follicles into the scalp.

Please refer to FIG. 7. For the purpose of implanting the hair follicles more efficiently, a plurality of micro-implanter for hair follicles 10, each of which having one hair follicle 30 held therein, are inserted into multiple mini implanting slits 32 cut on the bald scalp 31 in one or two rows, and the hair follicles 32 are pushed by the plungers 11 into the mini implanting slits 32 one by one.

The micro-implanter for hair follicle 10 of the present invention has the advantages of small volume and low weight to allow the hair follicle 30 to be quickly implanted into the mini implanting slit 32 cut on the bald scalp 31. In the course of implanting, the micro-implanter for hair follicle 10 does not directly touch a hair root portion of the hair follicle 30 to avoid damaging the hair follicle 30. Moreover, since the hair follicle 30 is positioned in the hair follicle holding tube 20 before being implanted into the mini implanting slit 32, the hair follicle 30 is protected against breaking and death in the event of repeated implantation.

The present invention has been described with a preferred embodiment thereof and it is understood that many changes and modifications in the described embodiment can be carried out without departing from the scope and the spirit of the invention that is intended to be limited only by the appended claims.

What is claimed is:

1. A micro-implanter for hair follicle for implanting hair follicles into mini implanting slits cut on a bald scalp, comprising:
    a plunger having an upper end and a lower end wherein the lower end has an outwardly extending stopper that extends radially outwardly;
    a hair follicle holding tube having a beveled surface at a lower end thereof and defining an axial bore, in which said plunger is axially movably received, said holding tube being capable of receiving a hair follicle which is positioned below the lower end of said plunger;
    an open slot provided in said holding tube extending axially upward from said lower end for a predetermined distance, wherein said open slot receives the outwardly extending stopper of the plunger such that the outwardly extending stopper is guided by the open slot so as to move upwardly and downwardly along the hair follicle holding tube;
    wherein the outwardly extending stopper includes a downwardly extending tapered bottom, the tapered bottom being offset longitudinally from the lower end of the plunger so as to limit a depth by which a hair follicle is implanted into the mini implanting slit;
    whereby when said hair follicle holding tube is inserted into one of the mini implanting slits on the scalp, a force may be applied to the upper end of said plunger to thereby place said hair follicle in said hair follicle holding tube into said mini implanting slit until the tapered bottom of the outwardly extending stopper contacts the scalp and the hair follicle is completely implanted into said mini implanting slit.

2. The micro-implanter for hair follicle as claimed in claim 1, wherein said hair follicle holding tube has a tapered and narrowed section at the lower end thereof adjacent the bevel.

* * * * *